(12) United States Patent
Billack et al.

(10) Patent No.: US 8,372,869 B2
(45) Date of Patent: Feb. 12, 2013

(54) PROCESS FOR THE TREATMENT OF BACTERIAL INFECTIONS USING 2-PHENYL-1,2-BENZISOSELENAZOL-3(2H)-ONE 1-OXIDE

(76) Inventors: Blase Christopher Billack, Clifton, NJ (US); Aneta Marta Billack, Clifton, NJ (US)

( * ) Notice: Subject to any disclaimer, the term of this patent is extended or adjusted under 35 U.S.C. 154(b) by 412 days.

(21) Appl. No.: 12/381,120

(22) Filed: Mar. 9, 2009

(65) Prior Publication Data

US 2010/0227899 A1 Sep. 9, 2010

Related U.S. Application Data

(60) Provisional application No. 61/068,068, filed on Mar. 5, 2008.

(51) Int. Cl.
*A01N 43/64* (2006.01)
*A61K 31/41* (2006.01)

(52) U.S. Cl. ...................................................... 514/359
(58) Field of Classification Search ................... 514/359
See application file for complete search history.

(56) References Cited

U.S. PATENT DOCUMENTS

2009/0005422 A1* 1/2009 Holmgren et al. ............ 514/338

OTHER PUBLICATIONS

Holmgren et al. (US Patent Application 2009/0005422 A1) in view of Masumoto et al. ("The Reaction of Ebselen with Peroxynitrite" Chem. Res. Toxicol. 1996, 9, 262-267).*

Muller et al. ("The electrochemical oxidation of 2-phenyl-1,2-benzisoselenazol-3(2H)-one and its derivatives. A study of the electrode process in dried acetonitrile at conventional electrodes and microelectrodes" Journal of Electroanalytical Chemistry, 407, 1996, 175-181).*

* cited by examiner

*Primary Examiner* — Yong Chong (57) ABSTRACT

The subject invention demonstrates a novel antibacterial activity for 2-phenyl-1,2-benzisoselenazol-3(2H)-one 1-oxide, commonly referred to as ebselen se-oxide, and is directed to the treatment of bacterial infections by administration of an effective amount of said compound. Bacterial infections include those infections which are either systemic or superficial in nature. The treatment is intended for a variety of animals, such as premature neonates to adult humans. Administration of ebselen se-oxide to treat superficial bacterial infections may be performed by a topical application, such as via an ointment, a spray, a cream, a mouth wash, an eye drop solution, an ear drop solution, a soap, a gel, or a lotion. In addition, an antibacterial capsule can be administered orally or intravaginally. Administration of ebselen se-oxide to treat systemic bacterial infections may be performed by an intravenous route, a rectal route, an intranasal route, an oral route, an intramuscular route, or by inhalation. Administration of said compound may also be achieved via aerosol, which can be generated by a nebulizer. Ebselen se-oxide may be administered alone, or with a carrier such as dimethylsulfoxide (DMSO), an alcohol, or other suitable carrier. The effective daily amount of ebselen se-oxide is from about 1 μg/kg to 10 mg/kg of body weight.

8 Claims, 5 Drawing Sheets

Minimal inhibitory concentration of ebselen se-oxide determined using drug-resistant S. aureus strains

| S. aureus strain | MIC (µM) |
|---|---|
| ATCC 33592[a] | <3.5 |
| NARSA VRS1[b] | <3.5 |

[a] resistant to methicillin
[b] resistant to both methicillin and vancomycin

FIG. 5

Effect of ebselen and ebselen se-oxide on the viability of A-431 human skin cells $LC_{50}$ (μM)

| ebselen | ebselen se-oxide |
|---|---|
| >50 | >50 |

PROCESS FOR THE TREATMENT OF BACTERIAL INFECTIONS USING 2-PHENYL-1,2-BENZISOSELENAZOL-3(2H)-ONE 1-OXIDE

RELATED APPLICATIONS

This application claims benefit of provisional application No. 61/068,068, filed on Mar. 5, 2008.

BACKGROUND OF THE INVENTION

Introduction

The Gram-stain technique is commonly used to classify bacteria into one of two broad classes (1,2). The first of these classes, designated as Gram-positive bacteria, includes those bacteria which, upon exposure to a crystal violet dye, retain the dye and appear colored upon microscopic examination. The second broad class, known as Gram-negative bacteria, includes those bacteria which, upon exposure to the crystal violet dye, do not retain the dye and, upon examination under the microscope, appear devoid of Gram-stain.

Although many types of bacteria have been found to be pathogenic to humans and other mammals, a defined list of said pathogens include bacterial species belonging to the genus *Staphylococcus, Escherichia, Mycobacterium, Micrococcus, Streptococcus, Enterococcus, Staphylococcus, Clostridium, Klebsiella*, and *Psuedomonas* (3). Bacterial species within each respective genus can cause devasting human pathologies including, but not limited to, toxic shock syndrome and wound infections (Staphylococcus), urinary tract infections and diarrhea (*Escherichia*), tuberculosis and leprosy (*Mycobacterium*), pneumonia and neonatal infection (*Streptococcus*) and tetanus and botulism (*Clostridium*) (3,4). Of those mentioned here, bacterial species belonging to genus *Escherichia, Klebsiella*, or *Pseudomonas* are classified as Gram-negative microbes, whereas species belonging to genus *Staphylococcus, Micrococcus, Streptococcus, Enterococcus, Staphylococcus*, and *Clostridium* are classified as Gram-positive. Although bacterial species belonging to *Mycobacterium* do not retain the crystal violet Grain-stain, they are classified as an acid-fast Gram-positive due to their lack of an outer cell membrane (5).

With respect to the treatment of patients infected with pathogenic bacteria, many classes of antibacterial agents are known, including the fluoroquinolones and quinolones, chloramphenicol, monobactams, polymyxins, cephalosporins, tetracyclines, sulfonamides, aminoglycosides, glycopeptides, macrolides, trimethoprim and chloramphenicol. The fundamental mechanisms of action of these antibacterial agents vary (6). Moreover, not all antimicrobial agents are equally effective. To this end, whereas some antimicrobial agents exhibit a broad spectrum of activity and are effective against both Gram-negative and Gram-positive microbes, such as the levofloxacin, a fluoroquinolone antibiotic, other types of antibacterial agents are more narrow in activity and are specific against only one type of Gram-stain class (6). Therefore, knowledge of the type of bacteria responsible for a particular infection enables a physician to determine the most appropriate type of antimicrobial agent which is best suited to combat a particular type of microbe.

Despite the many distinct types of antibiotics mentioned in the preceding paragraph, some bacterial infections are pharmacologically challenging. This is mainly because bacterial resistance to several important antibacterial agents has been documented, posing a serious threat to the public health (7,8).

In particular, drug-resistant strains of bacterial species belonging to genus *Staphylococcus*, genus *Mycobacterium* and genus *Streptococcus* have been discovered (9-12), making treatment of such resistant bacteria difficult to eradicate. Examples of such strains are methicillin-resistant *Staphylococcus aureus* (MRSA) (11), penicillin-resistant *Streptococcus pneumoniae* (9), extensively drug-resistant *Mycobacterium tuberculosis* (10), and tetracycline-resistant *Escherichia coli* (13). Resistance to other antimicrobial agents, such as to chloramphenicol, aminoglycosides and cephalosporins, has also been observed (6). Drug resistance in these microbes usually involves the enzymatic inactivation of the antibiotic by hydrolysis or by formation of inactive metabolites or derivatives.

In response to the emergence of bacteria resistant to standard antibacterial treatments, the development of novel antibacterial agents is urgently required. To this end, the present patent application provides evidence to demonstrate that the synthetic compound 2-phenyl-1,2-benzisoselenazol-3(2H)-one 1-oxide, represented by formula I and commonly referred to as ebselen se-oxide (14), exhibits antibacterial activity. This is a novel property concerning said compound. Furthermore, the invention reports on a novel use of said compound in the treatment of bacterial infections in humans and other warm-blooded animals. The present invention is based on the observations presented in the Experimental Findings section of this application which demonstrate the antibacterial effects of ebselen se-oxide towards a Gram-positive strain of *Staphylococcus aureus* and a Gram-negative strain of *Escherichia coli*. The precise mode of antibacterial action of ebselen se-oxide remains unknown. However, as will be discussed later, it is likely that the propensity of the tetravalent selenium atom of ebselen se-oxide to interact with the amino acid L-cysteine may contribute to the observed antibacterial activity reported here. Ebselen se-oxide is not commercially available but may be produced by reacting equimolar amounts of ebselen with peroxynitrite according to a process described by H. Masumoto and H. Sies in 1996 (14). Moreover, the tetravalent selenium atom of ebselen se-oxide (see Formula I) sets it apart from other benzisoselenazol-bearing compounds within the art.

(I)

SUMMARY OF THE INVENTION

This invention demonstrates that the synthetic compound 2-phenyl-1,2-benzisoselenazol-3(2H)-one 1-oxide, commonly referred to as ebselen se-oxide and represented by formula I, exhibits a novel antibacterial activity and can be used as an active agent in a process for the treatment of diseases caused by bacterial infections. The process is meant to be used in a wide variety of warm-blooded animals including premature neonates to adult humans.

The process entails administering to said animal or human being a pharmaceutical preparation comprising 2-phenyl-1, 2-benzisoselenazol-3(2H)-one 1-oxide, commonly referred to as ebselen se-oxide, as the active agent in an amount of 1 to 1500 mg per day.

Administration of ebselen or ebselen se-oxide to treat superficial bacterial infections may be performed by topical route, such as via an ointment, spray, eye drop solution, cream, mouth wash, soap or lotion. Administration of the subject compound to treat systemic bacterial infections may be performed by an intravenous route, a rectal route, an intranasal route, an oral route, an intramuscular route, or by inhalation.

Ebselen se-oxide may be administered alone, or with a carrier such as dimethysulfoxide (DMSO), an alcohol, or other suitable carrier. The effective daily amount of each of the said compounds is from about 1 µg/kg to 10 mg/kg of body weight. The dosages may be administered daily as a single dose or in several partial doses.

BRIEF DESCRIPTION OF FIGURES

FIG. 3: Representative figure depicting thin-layer chromatographic analysis of the products formed by reacting (30 mM) ebselen se-oxide with (30 mM) L-cysteine: Lane 1, ebselen se-oxide; Lane 2, ebselen se-oxide overspotted with L-cysteine; Lane 3, L-cysteine. L-cysteine was visualized with ninhydrin reagent followed by warming at 70° C. in an oven. Spots representing unreacted ebselen se-oxide (dotted circles) were visualized after an exposure to iodine vapors. In lane 2, notice the disappearance of the L-cysteine spot and the appearance of a new, slower migrating, spot than ebselen se-oxide, representing a condensation product of L-cysteine and ebselen se-oxide. As ebselen se-oxide was dissolved in DMSO prior to spotting, a hazy DMSO front was observed on the TLC plate in lanes in which the ebselen se-oxide compound was spotted (lanes 1 and 2).

DETAILED DESCRIPTION OF THE INVENTION

One embodiment of the subject invention relates to a process for the treatment of bacterial infections which involves the administration of an effective amount of 2-phenyl-1,2-benzisoselenazol-3(2H)-one 1-oxide, also referred to as ebselen se-oxide, as the active antibacterial agent. The treatment is intended for a variety of warm-blooded mammals afflicted by bacterial infections, such as premature neonates to adult humans. The use of ebselen se-oxide to treat bacterial infections has not been reported to date and thus represents a novel way to combat diseases caused by bacterial pathogens.

Whereas ebselen se-oxide can inhibit the growth of Gram-positive and Gram-negative strains of bacteria, the said compound is particularly useful for inhibiting the growth of disease-causing Gram-positive bacteria.

Ebselen se-oxide as the active agent is to be administered in an amount ranging from 1 to 1500 mg per day. It can be used to treat systemic infections, in which the bacterial pathogens have gained access to the circulatory system, and those which are localized to a specific body compartment that is exposed to the environment such as the skin, the ears, the throat, the eyes, the lungs, the fingers, the fingernails, the toes, the toenails, the nose, the vagina, the penis, or the mouth.

Examples of systemic or localized bacterial infections which can be reduced or blocked by ebselen se-oxide include those caused by species of bacteria belonging to the genus *Staphylococcus, Escherichia, Mycobacterium, Micrococcus, Streptococcus, Enterococcus, Staphylococcus, Clostridium, Klebsiella, Psuedomonas* or *Chlamydia*, as well as many others.

The said invention provides for a treatment against bacterial infections and is intended for a variety of mammals, such as premature neonates to adult humans. Moreover, the said invention is useful in humans who are predisposed to bacterial infections, such as those with immunodeficiency disorders and those who are immunosuppressed due to chemotherapy or other causes.

In addition, the invention is intended for use in situations wherein the disease-causing pathogen is a bacterial isolate with documented resistance to standard antibacterial agents that are currently in clinical use. Examples of drug-resistant bacterial isolates include bacterial strains of methicillin-resistant *Staphylococcus aureus* (MRSA), vancomycin-resistant *Staphylococcus aureus* (VRSA), penicillin-resistant *Streptococcus pneumoniae*, extensively drug-resistant *Mycobacterium tuberculosis*, and tetracycline-resistant *Escherichia coli*

Due to the hydrophobic nature of ebselen se-oxide, the compound is also useful against bacterial infections of the brain and spinal cord, such as bacterial meningitis.

Administration of ebselen se-oxide to treat localized bacterial infections may be performed by a topical application, such as via an ointment, a spray, a cream, a mouth wash, an eye drop solution, an ear drop solution, hand soap, a body wash, a shampoo, or a lotion. In addition, an antibacterial capsule can be administered orally or intravaginally. A water-soluble capsule with a soft gelatin shell is preferred type of capsule to be used for intravaginal administration.

Administration of ebselen se-oxide to treat systemic bacterial infections may be performed by an intravenous route, a rectal route, an intranasal route, an oral route, an intramuscular route, or by inhalation. Administration of said compound may also be achieved via aerosol, which can be generated by a nebulizer, or by instillation directly into the lung.

Ebselen se-oxide may be administered alone, or with a carrier such as dimethylsulfoxide (DMSO), an alcohol, or other suitable carrier. Such carriers are well known in the art, and the specific carriers employed may be varied upon factors such as size of the subject being treated, treatment dose, and the like.

The effective daily amount of ebselen se-oxide is from about 1 µg/kg to 10 mg/kg of body weight.

The dosages may be administered daily as a single dose or in several partial doses, up to 4 times daily, until the desired daily dosage is fully administered. The time frame over which the said compound is administered may vary as is well known in the art to achieve the desired results. For example, ebselen se-oxide may be administered as an intravenous infusion from about 10 minutes to about 1 hour per treatment regimen, 3 or 4 times daily, or until the daily dosage is fully administered.

For the purpose of the invention, all forms of ebselen se-oxide, regardless of source, would follow a treatment similar to that described above.

While not being bound by any specific mode of bacterial inhibition, it is believed that the growth-inhibitory effect of ebselen se-oxide towards bacteria may be related, at least in part, to its interaction with one or more key cysteine residues important for normal bacterial growth. An alternate possibility to explain the antibacterial activity of ebselen se-oxide is that bacteria possess the ability to convert ebselen se-oxide to ebselen. If this were to occur, ebselen se-oxide would be acting within bacteria in a manner akin to an ebselen prodrug. To the present date, the use of ebselen prodrugs to combat bacterial infections has not been reported. Consequently, the likelihood of this latter possibility contributing to the antibacterial nature of ebselen se-oxide is unknown.

The subject invention is also directed to the preventative treatment of infections by the bacteria mentioned above. To this end, ebselen se-oxide may be utilized as a prophylactic agent to prevent the development of bacterial infections, particularly in immunosuppressed and immunocompromised human populations who are at high risk of such infections. In specific terms, prophylaxis against said bacterial infections may be achieved by the administration of an effect amount of said inhibitors in the form of lotions, soaps, and creams.

The subject invention is also directed to the preservation of foods from spoilage by bacterial microbes through the application of an effective amount of ebselen se-oxide to the surface of fruits and vegetables. Application of said inhibitor can be achieved by spraying said fruit or vegetable with a solution containing between 0.1 and 50% of ebselen se-oxide.

The following Example is merely for illustrative purposes and is not intended to limit the invention. All parts are parts by weight, unless otherwise indicated.

EXAMPLE 1

Treatment of a Bacterial Infection of the Eye Using Ebselen Se-Oxide as the Active Ingredient Ebselen se-oxide is topically administered to the eye in the form of an aqueous solution or suspension. Preferably the suspension contains 0.001 to 10 percent by weight, most preferably between about 0.005 and about 4% by weight, of ebselen se-oxide.

In order to enhance the solubility of ebselen se-oxide in the ocular composition, pharmaceutically acceptable eye-compatible adjuvants, such as propylene glycol or glycerine, in amounts between 0.01 and 30% weight percent, based on the total weight of the composition, may be employed. Furthermore, conventional pharmaceutical excipients, such as sodium borate, boric acid, sodium citrate and the like may be present in amounts between about 0.01 and 3 weight percent, based on the total weight of the composition. In addition, opthamologically acceptable preservatives, such as sodium edetate, sorbic acid and the like may be present in amounts between about 0.001 and 0.1 weight percent, based on the total weight of the composition. If desired, the osmolality of the resulting composition may be adjusted to ensure that the composition is substantially isotonic. Preferably, the pH of the aqueous composition should be in the range of a pH of 5 to a pH of 7.5.

The dosages of the eye drop solution containing ebselen se-oxide as the active antibacterial agent may be administered daily as a single dose of 1-20 drops per day or in several partial doses of 1-5 drops, up to 4 times daily, until the desired daily dosage is fully administered.

As observed in formula I, ebselen se-oxide represents a benzisoselenazol-dione compound. Other benzisoselenazol-diones similar to the structure depicted in formula I may also exhibit antibacterial activity. Therefore, in another embodiment of the invention, analogs of ebselen se-oxide in which the 2-phenyl ring is either (a) substituted with one or more chlorine atoms, or (b) replaced by a pyridinyl ring may also exhibit potent antibacterial activity and may serve as active ingredients to treat bacterial infections.

Experimental Findings

Materials and Methods
1. Bacterial strains and test compound

A Gram-negative *Escherichia coli* strain, DH5(alpha), was purchased from Invitrogen (Cat #18265-017; Carlsbad, Calif.) and a Gram-positive *Staphylococcus aureus* strain, positive for catalase and coagulase, was purchased from Ward's Natural Science (Cat #85V1178; Rochester, N.Y.). *S. aureus* strain ATCC 33592 is a clinical isolate which is resistant to methicillin and which was obtained from the American Type Culture Collection (Manassas, Va.). *S. aureus* strain NARSA VRS 1 is a clinical isolate which is resistant to both methicillin and vancomycin and which was obtained from Focus Technologies, Inc. (Herndon, Va.). These bacterial strains were used to test the antibacterial activity of ebselen se-oxide. To prepare ebselen se-oxide, an adequate amount of said compound was dissolved in 0.5 mL of dimethylsulfoxide (DMSO) to give a 30.0 mM stock solution.

2. Media and growth conditions

Luria Broth (LB) was used to for the culturing of both bacterial strains. LB culture medium was prepared by dissolving 15.5 g of Difco Luria Broth Base, Miller (BD, Franklin Lakes, N.J.) into 1 L of distilled $dH_2O$ and then autoclaving the solution at 121° C. for 15 minutes.

3. Assay to Test the Antibacterial Effect of Ebselen Se-Oxide

Bacterial growth, in the absence or presence of ebselen se-oxide, was assessed by light-scattering at 550 nm. In separate experiments, bacterial cells of either the *Staphylococcus aureus* or the *Escherichia coli* strain were inoculated into polypropylene tubes containing 5 mL of LB medium to obtain an initial optical density at 550 nm ($OD_{550}$) of ~0.005, as determined using a spectrophotometer (UV 160U, Shimadzu Corp., Kyoto, Japan). Respective cell suspensions were then cultured in the presence (0.1, 1, 3, 10 or 30 μM) or absence (control) of ebselen se-oxide in duplicate and shaken in a shaking incubator (Shaker MaxQ A4000, Barnstead Lab-Line, Melrose Park, Ill.) set at 200 rpm and 37° C. for 18-20 hr. The concentration of DMSO carrier did not exceed 0.1% (vol/vol) in any samples.

4. Thin Layer Chromatography (TLC)

TLC was carried out in a glass chamber lined with Whatman No. 2 filter paper (Whatman Inc, Florham Park, N.J.), and pre-saturated with the mobile phase (1-propanol/water, 7+3, by volume) for 2 hr. The samples (34.5 mM ebselen se-oxide, 30.0 mM L-cysteine, and a 1:1 mixture of each compound with L-cysteine) were spotted with capillary tubes along a line drawn 2 cm above one of the edges of a 20×20 cm silica gel Whatman polyester plate (Whatman Ltd. Maidston, Kent, England). The plate was placed in the glass chromatographic chamber, and allowed to develop until the mobile phase reached a distance of 14 cm from the starting line. The TLC plate was dried in a 70° C. oven and sprayed lightly with 0.2% ninhydrin in acetone, and then placed back into the oven until the appearance of spots representing L-cysteine. After the ninhydrin treatment, the TLC plate was exposed to iodine vapors in a closed chamber for 2 min and any dark spot, corresponding to unsaturated or aromatic compounds, was circled with a pencil. As a confirmatory step, the plate was also examined under short wavelength UV light for the presence of fluorescence-quenching spots.

5. Broth Microdilution Susceptibility Testing of Drug-Resistant Strains of *S. aureus*:

Note that all susceptibility assays were performed in triplicate wells using sterile flat-bottom 96-well microtiter plates. In brief, three to five colonies of *S. aureus* strains ATCC 33592 or NARSA VRS1 greater than 1 mm in diameter were selected from stock plates, suspended in Mueller Hinton Broth, and adjusted to obtain an initial inoculum $OD_{550}$ nm of ~0.010 on a spectrophotometer. Stock solutions of ebselen se-oxide were prepared in 100% dimethyl sulfoxide (DMSO) and then diluted accordingly in Mueller Hinton Broth to obtain the ×2 drug concentration (50, 25, 12.5 or 6.25 µM). Each well of the microplate containing 100 µl of the appropriate ebselen se-oxide solution (2× final concentration) was inoculated with 100 µl of the inoculum suspension, yielding final ebselen se-oxide concentrations ranging from 3.125 µM to 25 µM. The growth control wells each contained 100 µl of the inoculum suspension, 100 µl of Mueller Hinton containing 0.1% DMSO vehicle. Sterility control wells contained 200 µl of Mueller Hinton. After 24 (±4) hr of incubation at 35-37° C., the MIC (minimum inhibitory concentration) for ebselen se-oxide was determined for each strain visually by comparing the turbidity of the triplicate treatments to that observed for drug-free growth control wells. For each strain, the MIC was defined as the lowest concentration showing 100% growth inhibition, relative to controls, in all three wells of a given treatment.

6. Effect of Ebselen and Ebselen Se-Oxide on the Viability of Human Skin Cells:

Confluent 24-well microtiter plates were used to examine the effects of ebselen or ebselen se-oxide on the viability of human A-431 skin cells. On the day cells were treated, media was removed from the wells and replaced with 0.5 ml of serum- and phenol red-free DMEM containing either 0 (control), 12.5, 25 or 50 µM of ebselen or ebselen se-oxide. Cells were then incubated for 24 hr at 37° C. After incubation, the MTT viability assay was performed. This assay measures the conversion of 3-[4,5-dimethylthiazol-2-yl]-2,5-diphenyl tetrazolium bromide (MTT) into a colored product in living cells. The optical density of this purple formazan product in the cell culture medium was then measured spectrophotometrically at 570 nm and cell viability was determined as described by Mosmann (15).

Results

7. Effect of Ebselen Se-Oxide on the Growth of Gram-Negative and Gram-Positive Bacteria To determine the effect of ebselen se-oxide on the growth of bacteria, a Gram-negative bacterial strain of *Escherichia coli* and a Gram-positive strain of *Staphylococcus aureus* were seeded at a low optical density in LB medium containing 0-30 µM ebselen se-oxide. The effect of ebselen se-oxide on bacterial growth was assessed after 18-20 hours of culturing in a shaking incubator set at 37° C. by measuring the optical density of the culturing medium at 550 nm. Ebselen se-oxide inhibited the growth of the Gram-positive strain (FIG. 1) and of the Gram-negative strain (FIG. 2). In both strains, the inhibition of bacterial growth was found to be dependent on the concentration of ebselen se-oxide used during the incubation. As revealed in FIG. 1, the inhibitory concentration of ebselen se-oxide required to inhibit the growth of *Staphylococcus aureus* to that of 50% of the untreated control, a value known as the IC50, was determined to be ~0.6 µM. It is worthy to note that the IC50 of ebselen se-oxide towards *Escherichia coli* cells was observed to be ~17.0 µM.

Figure 3:
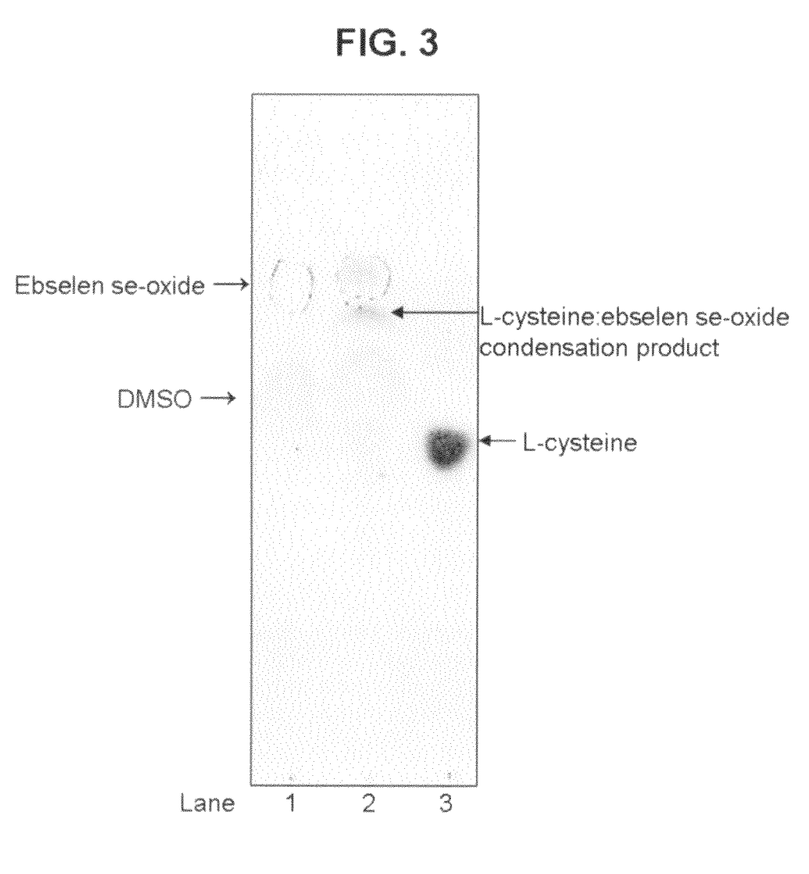

8. Thin Layer Chromatography of Ebselen Se-Oxide, L-Cysteine, and a Combination of Both Although the antibacterial mechanism of ebselen se-oxide remains unknown, it is possible that the tetravalent selenium atom within the structure of ebselen se-oxide depicted in formula I can modify critical cysteine residues necessary for normal bacterial growth and survival. Therefore, to determine whether or not ebselen se-oxide exhibits a propensity to modify or react with L-cysteine, a thin layer chromatography (TLC) analysis was performed. Equal volumes of 30 mM solutions of ebselen se-oxide and L-cysteine were repeatedly spotted on the same application point of the TLC plate to find out whether the two compounds will interact in situ in a spontaneous and rapid manner. Ebselen se-oxide and L-cysteine solutions were also separately spotted alongside the reaction mixtures for comparative purposes. A representative TLC chromatograph is depicted in FIG. 3. The dark spot detected by an exposure to iodine vapors, and located at the top of lane one (circled), is ebselen se-oxide. The lone ninhydrin spot towards the bottom of lane three is L-cysteine. The ninhydrin-positive spot in lane two which migrates more slowly than the spot for ebselen se-oxide (circled) but ahead of the spot for L-cysteine is ascribed to an ebselen-L-cysteine condensation product.

Figure 4:
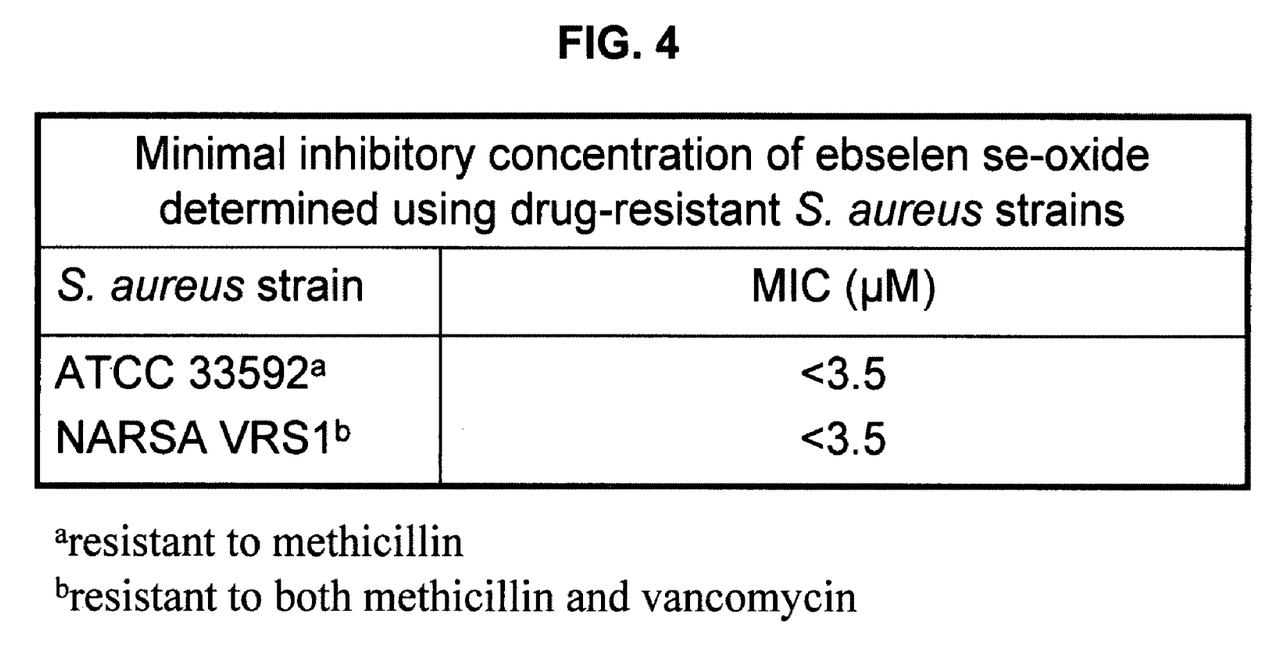
FIG. 4: Minimal inhibitory concentration of ebselen se-oxide determined using drug-resistant *S. aureus* strains
Figure 5:
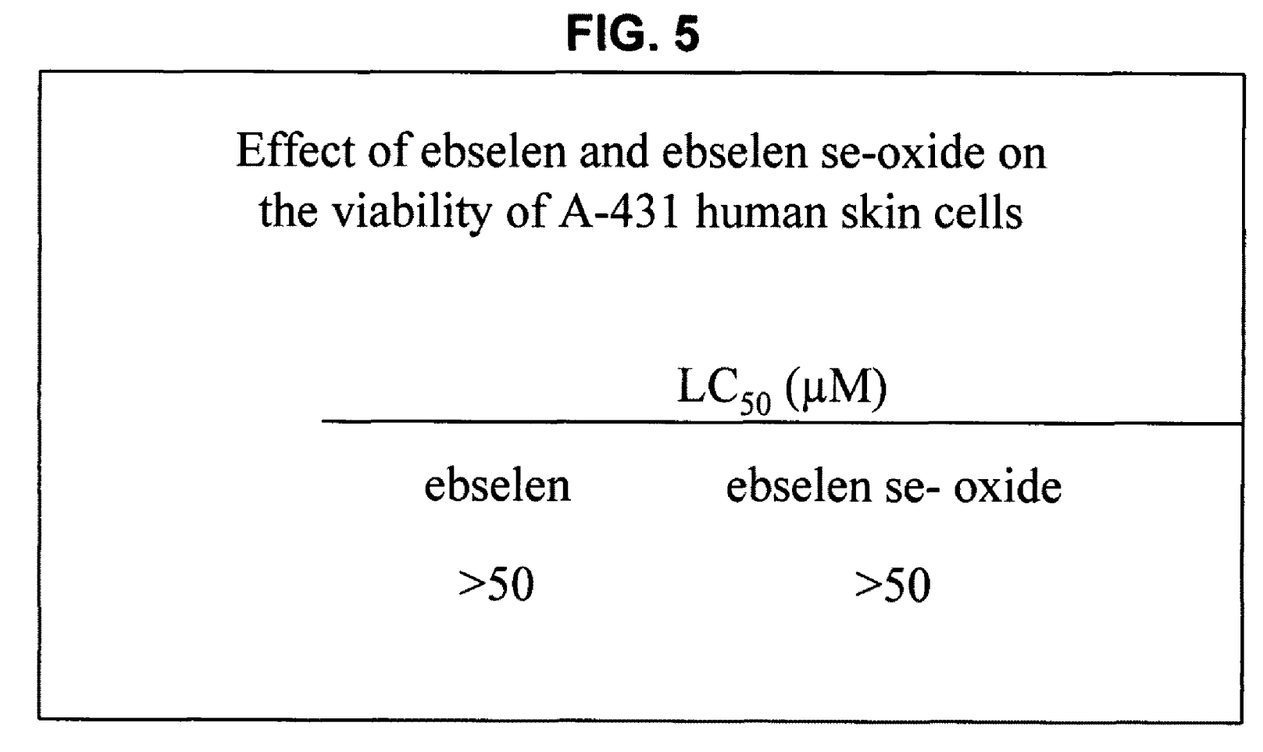
FIG. 5: Effect of ebselen and ebselen se-oxide on the viability of A-431 human skin cells

9. Evaluation of the Antibacterial Activity of Ebselen Se-Oxide in Drug-Resistant *S. aureus* Strains Using a methicillin-resistant strain (ATCC 33592), as well as a strain of *S. aureus* resistant to both methicillin and vancomycin (VRSA NRS1), MIC values for ebselen se-oxide in Mueller Hinton medium were obtained. Recall from above that the MIC is defined as the lowest concentration showing 100% growth inhibition, relative to controls, in all three wells of a given treatment. As can be seen in FIG. 5, ebselen se-oxide exhibited potent antibacterial efficacy in vitro, as determined by MIC values in the low micromolar range (FIG. 4). The observation that ebselen se-oxide can inhibit such drug-resistant bacterial growth is novel to the art.

10. Assessment of the Effect of Ebselen and Ebselen Se-Oxide on the Viability of Human Skin Cells:

To determine whether or not ebselen or ebselen se-oxide can exhibit a cytotoxic effect upon human cells, A-431 human skin cells were incubated at 37° C. for 24 hr in the absence or presence of 12.5, 25, or 50 µM of ebselen or ebselen se-oxide. The MTT assay was used to determine cell viability and the $LC_{50}$ value for ebselen se-oxide in these cells was evaluated. Note that the $LC_{50}$ value represents the lethal concentration of an agent which kills 50% of the cell population. As shown in FIG. 5, neither compound was toxic to the skin cells over the range of concentrations tested.

Discussion of Findings

Figure 1:
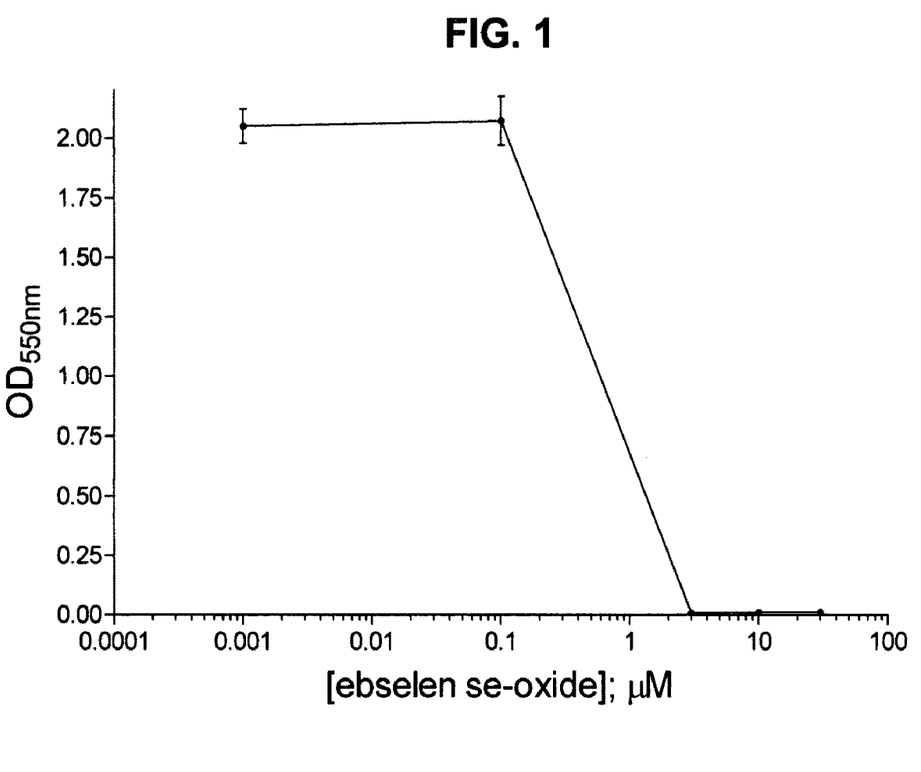
FIG. 1: Representative figure depicting the growth-inhibitory effect of ebselen se-oxide in *Staphylococcus aureus*. Data points represent the mean±the standard deviation of duplicate samples. This experiment was repeated two times with similar results.
Figure 2:
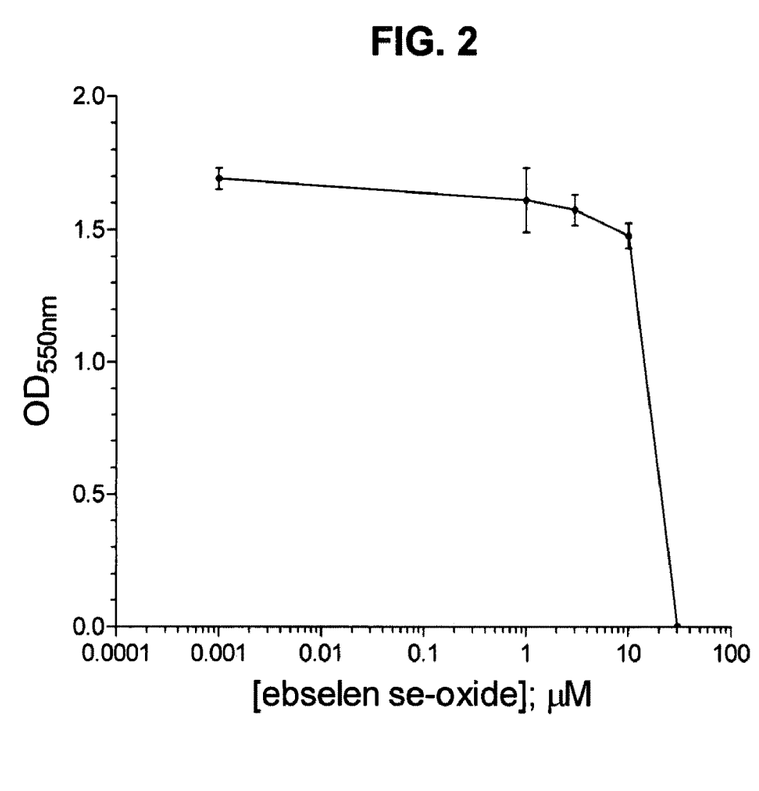
FIG. 2: Representative figure depicting the growth-inhibitory effect of ebselen se-oxide in *Escherichia coli*. Data points represent the mean±the standard deviation of duplicate samples. This experiment was repeated two times with similar results.

From the results graphically depicted in FIG. 1 and FIG. 2, the growth-inhibiting action of ebselen se-oxide was found to be concentration-dependent. In addition, based on the $IC_{50}$ values gathered in this experiment, it is evident that while the antimicrobial activity of ebselen is directed toward microbes representing a wide range of types, it is more potent against Gram-positive bacteria ($IC_{50}$=~0.6 µM) than against Gram-negative bacteria ($IC_{50}$=~17.0 µM). These data not only confirm a novel antibacterial activity of ebselen se-oxide, but they also point to the existence of variability in the susceptibility to its antimicrobial actions among different bacterial species. The differences in sensitivity of Grain-negative bacteria to ebselen se-oxide in comparison to Gram-positive bacteria may stem from surface structural differences among these organisms. Thus, while the surface of Gram-positive bacteria is coated with a rather thick and relatively hydrophilic cell wall that protects them from their external environment and osmotic stress while allowing the flux of small molecules, Gram-negative bacteria surround their plasma membrane by a thin cell wall of peptidoglycan, a large periplasmic space with digestive enzymes, and a hydrophobic outer membrane of lipopolysacharide, protein, and phospholipids, at the periphery. Hence, because of these structural differences ebselen se-oxide may be able to reach the plasma membrane Gram-positive bacteria more readily than that of Gram negative bacteria. In addition, the observation that ebselen se-oxide exhibits an antimicrobial activity towards clinically relevant isolates of *S. aureus* which exhibit resistance to methicillin and vancomycin (FIG. 4), while showing no toxicity towards human cells (FIG. 5), is novel to the art.

Although the mechanism by which ebselen se-oxide achieves antibacterial activity is not presently understood, the said antibacterial activity may be related to a propensity to interact with vital cysteine residues within or on the surface of bacteria. To demonstrate this assumption, an in vitro experiment was conducted on ebselen se-oxide whereby this compound was allowed to react with L-cysteine at ambient temperature at the starting point of a TLC plate, followed by development of the plate with a suitable solvent (FIG. 3). Since no spot resembling L-cysteine was apparent in lane two, it is concluded that all the L-cysteine had reacted with ebselen se-oxide to form the new ebselen se-oxide:L-cysteine condensation product and that some unreacted ebselen se-oxide had been left behind. This finding not only shows that ebselen se-oxide can modify L-cysteine but also suggests that the stoichiometry of the interaction of L-cysteine with ebselen se-oxide is not 1:1; but rather 2:1 or greater.

In summary, the data presented in the Experimental Findings portion of this application demonstrate that ebselen se-oxide exhibits a growth-inhibitory effect on bacteria and that said activity may be related, at least in part, to interaction with or modification of one or more key cysteine residues important for normal bacterial growth. An alternate explanation to explain the observed antibacterial activity of ebselen se-oxide may stem from a conversion of the ebselen se-oxide to ebselen, a documented antibacterial agent (16, 17, 18), within or on the surface of bacteria. The conversion of ebselen se-oxide to ebselen is a reaction that readily occurs in the presence of reducing equivalents (14). Thus, the possibility that ebselen se-oxide acts as prodrug which gets converted to ebselen in bacteria is one that bears further exploration.

REFERENCES

1. Bergey D H. *Bergey's Manual of Determinative Bacteriology*, 9th ed. In: Holt J G, Krieg N R, Sneath PHA. Lippincott Williams & Wilkins; Baltimore, 1993.
2. Jacobson W. Gram's discovery of his staining technique. J Infect 1983; 7:97-101.
3. Harvey R A, Champe P C, Fisher, B D. *Lippincott's Illustrated Reviews: Microbiology*, $2^{nd}$ ed. Lippincott, Williams and Wilkins; Baltimore, 2006.
4. Engelkirk P G, Burton G R. *Burton's Microbiology for the Health Sciences*, $8^{th}$ ed. Lippincott, Williams and Wilkins; Baltimore, 2006.
5. Salton, M R J. The relationship between the nature of the cell wall and the Gram stain. J Gen Microbiol. 1963; 30:223-35.
6. Howland R D, Mycek M J, Harvey R A, Champe P C. *Lippincott's Illustrated Reviews: Pharmacology* $3^{rd}$ Edition. Lippincott, Williams and Wilkins; Baltimore, 2006.
7. Ball P. Conclusions: the future of antimicrobial therapy—augmentin and beyond. Int J Antimicrob Agents 2007; 30S:S139-S141.
8. Cirz R T, Chin J K, Andes D R, de Crecy-Lagard V, Craig W, Romesberg F E. Inhibition of mutation and combating the evolution of antibiotic resistance. PLoS Biol 2005; 3:e176.
9. Van Bambeke F, Reinert R R, Appelbaum P C, Tulkens P M, Peetermans W E. Multidrug-resistant *Streptococcus pneumoniae* infections: current and future therapeutic options. Drugs 2007; 67:2355-2382.
10. Centers for Disease Control and Prevention. Extensively drug-resistant tuberculosis—United States, 1993-2006. MMWR Weekly 2007; 56:250-253.
11. Maree C L, Daum R S, Boyle-Vavra S, Matayoshi K, Miller L G. Community-associated methicillin-resistant *Staphylococcus aureus* isolates causing healthcare-associated infections. Emer Infect Dis 2007; 13:236-242.
12. Fille T M, Jr. *Streptococcus pneumoniae* and community-acquired pneumonia: a cause for concern. Am J Med 2004; 117 suppl 3A:39S-50S.
13. Chaudhury A, Nath G, Tikoo A, Sanyal S C. Enteropathogenicity and antimicrobial susceptibility of new *Escherichia* spp. J Diarrhoeal Dis Res 1999; 17:85-87.
14. Masumoto H, Sies H. The reaction of ebselen with peroxynitrite. Chem Res Toxicol 1996; 9:262-267.
15. Mosmann T. Rapid colorimetric assay for cellular growth and survival: application to proliferation and cytotoxicity assays. J Immunol Methods 1983; 65:55-63.
16. Chan G, Hardej D, Santoro M, Lau-Cam C, Billack B. Evaluation of the antimicrobial activity of ebselen: role of the yeast plasma membrane $H^+$-ATPase. J Biochem Mol Toxicol 2007; 21:252-264.
17. Nozawa K, Yokota T, Fujimoto T. Susceptibility of methicillin-resistant *Staphylococcus aureus* to the selenium-containing compound 2-phenyl-1,2-benzoisoselenazol-3 (2H)-one (PZ51). Antimicrob Agents Chemother 1989; 33:1388-1390.
18. Piętka-Ottlik M, Wójtowicz-Młochowska H, Kołodziejczyk K, Piasecki E, Młochowski J. New organoselenium compounds active against pathogenic bacteria, fungi and viruses. Chem Pharm Bull 2008; 56:1423-1427.

What is claimed is:

1. A method for treating a bacterial infection in a mammal in need thereof comprising administering to the mammal an effective amount of 2-phenyl-1,2-benzisoselenazol-3(2H)-one 1-oxide, or a pharmaceutically acceptable salt thereof, wherein the bacterial infection is caused by a species of bacteria belonging to the genus *Staphylococcus* or *Mycobacterium*.

2. The method of claim 1, wherein the mammal is a human neonate, a human adult, an immunosuppressed human, an immunocompromised human, a common farm animal or a common household pet.

3. The method of claim 1 or 2 wherein the bacterial infection is caused by an isolate of bacteria exhibiting resistance to methicillin, tetracycline, vancomycin, isoniazid, rifampin, or penicillin.

4. The method of claim 1, wherein administration to the mammal of an effective amount of 2-phenyl-1,2-benzisoselenazol-3(2H)-one 1-oxide is performed topically in the form of a cream, a gel, a lotion, an ointment, a foot spray, a nasal spray, a mouth wash rinse, an eye drop solution, a medicated shampoo, a soap, a douche, or an ear drop solution, or performed orally in the form of a tablet, a capsule, or a liquid, or performed intravaginally as a capsule or gel, or performed intratracheally by nebulization, or performed intravenously by infusion, or performed subcutaneously, or intrathecally, by injection.

5. The method of claim 1, wherein the bacterial infection results as a sequela of human exposure to an injurious chemical.

6. The method of claim 1, wherein the *Staphylococcus* infection results as a sequela of pharmacotherapy of a human patient with chemotherapeutic anticancer drugs.

7. The method of claim 1, wherein the *Staphylococcus* infection results from damage to skin or eye tissue caused by physical injury.

8. The method of claim 1, wherein the *Staphylococcus* infection results from insertion of a contaminated medical device into a body cavity, duct, or vessel.

\* \* \* \* \*